United States Patent [19]

Rosen et al.

[11] 4,220,142
[45] Sep. 2, 1980

[54] BEHAVIORAL SHAPING DEVICE FOR ELIMINATING NOCTURNAL SOUNDS

[75] Inventors: Raymond C. Rosen, both of 846 Hoes La., Piscataway, N.J. 08854; Linda J. Rosen, Piscataway; Zoltan L. Sisko, Middlebush, N.J.

[73] Assignees: Raymond C. Rosen; Linda J. Rosen, both of Piscataway, N.J.

[21] Appl. No.: 829,969

[22] Filed: Sep. 1, 1977

[51] Int. Cl.² ............................................. A61B 19/00
[52] U.S. Cl. .................................... 128/1 R; 340/575
[58] Field of Search ...... 128/1 R, 1 C, 136, DIG. 29, 128/716, 721, 905, 680–682; 35/22 R, 35 C; 340/407, 279, 511, 566, 575; 179/1 N, 1 VC; 364/419

[56] References Cited

U.S. PATENT DOCUMENTS

| | | | |
|---|---|---|---|
| 3,552,383 | 1/1971 | Krueger et al. | 128/682 |
| 3,553,401 | 10/1970 | Streu | 128/682 |
| 3,569,923 | 3/1971 | Naubereit et al. | 340/566 X |
| 3,593,703 | 7/1971 | Gunn | 179/1 R X |
| 3,713,128 | 1/1973 | Wong et al. | 340/566 |
| 3,778,552 | 12/1973 | Edinborgh | 179/1 N |
| 3,802,417 | 4/1974 | Lang | 128/DIG. 29 X |
| 3,930,494 | 1/1976 | Maurer et al. | 128/682 |
| 3,946,729 | 3/1976 | Hanna | 128/DIG. 29 X |
| 3,976,052 | 8/1976 | Jonginger et al. | 128/671 |
| 3,998,209 | 12/1976 | Mac Vaugh | 128/1 R |
| 4,012,852 | 3/1977 | Journot et al. | 35/35 C X |
| 4,020,567 | 5/1977 | Webster | 35/35 C |

Primary Examiner—Robert W. Michell
Assistant Examiner—Francis J. Jaworski
Attorney, Agent, or Firm—Peter L. Berger

[57] ABSTRACT

A behavior shaping device is disclosed for eliminating nocturnal sounds, such as snoring. The device comprises the generally well-known microphone amplifier and alarm means, with the alarm means being actuated when the input level is above a predetermined level. As part of the behavior shaping technique, a counter is provided to indicate the number of times the alarm is sounded in a predetermined time period to permit the lowering of the threshold level as the number of times the alarm is sounded decreases. Memory means are provided to store the counts generated in accordance with the time periods and to provide a display of the respective counts registered.

14 Claims, 2 Drawing Figures

BEHAVIORAL SHAPING DEVICE FOR ELIMINATING NOCTURNAL SOUNDS

BACKGROUND OF THE INVENTION

This invention relates to behavior modification devices, and more particularly, to a behavior shaping device intended to eliminate snoring, bruxism, somniloquoy, night coughing, and other aversive sleep sounds.

There are many conventional prior art devices which are intended to eliminate snoring, and these generally include microphones or transducers to sense a snoring sound and an alarm means to wake up the sleeper, causing him to be disrupted from his sleeping position, requiring the alarm to be turned off in order to allow the sleeper to return to bed. These devices, in many cases, fail to achieve the desired results, because the sleeper is able to believe that he is improving his performance nightly when, in fact, his performance is not getting any better, and may even be deteriorating. Further, these prior art devices do not operate to shape the subject's behavior.

PRIOR ART STATEMENT

Applicant, having conducted a novelty search, reports the following U.S. Pat. Nos. to be relevant: 3,998,209; MacVaugh, 3,593,703; Gunn et al, 3,696,377; Wall, 3,089,130; Wilson, 2,999,232; Wilson.

The patent to MacVaugh is directed to a snoring deconditioning system and is relevant in-so-far as it teaches behavior modification techniques. The subject is able to change the level required to trigger the alarm, but there is no relationship to his performance as to level changes. Quite a number of different deconditioning systems are illustrated, but the MacVaugh patent does not include any means to record the actual performance or the number of times the sleeper has actuated the alarm.

The remaining four patents to Gunn et al, Wall, Wilson '130, and Wilson '232 are all directed illustrative prior art anti-snoring devices which cause an alarm to be triggered when snoring is detected and require the sleeper to move or otherwise change his position to deactivate the alarm.

It has been discovered that the person seeking to change his behavior needs to have additional incentive for such change. Frequently, even though the sleeper is aroused to turn off an alarm, he may continue snoring as frequently as he previously had, without there being any material change.

The MacVaugh system is illustrative of classical operative behavior modification techniques.

OBJECTS OF THE INVENTION

An object of this invention is to provide an improved behavior modification device which minimizes or eliminates snoring or bruxism in a sleeper.

Another object of this invention is to provide such a device which is relatively foolproof, simple to operate, and effective.

Yet another object of this invention is to provide such a device which may be convenient to manufacture, susceptible of wide scale application, and be of moderate price.

Still another object of this invention is to provide a behavior shaping device to minimize nocturnal sounds.

Another object of this invention is to provide such a device which is capable of recording and storing a person's performance over any period of time.

Yet another object of this invention is to provide such a device in which the behavior modification techniques are substantially automatic, not requiring human intervention during sleep training.

Other objects, advantages, and features of this invention will become more apparent from the following description.

SUMMARY OF THE INVENTION

In accordance with the principles of this invention, the above objects are accomplished by providing a behavior modification device which comprises a transducer means responsive to sounds emanating from a sleeper, producing an output signal, means responsive to the production of the output signal to produce an aversive stimulus to wake the sleeper, maintaining the aversive stimulus, and register means to count the number of such output signals produced during a predetermined time period. Further means are provided to alter the level required to trigger the aversive stimulus, such as a buzzer or alarm, but the alteration of such a level may be accomplished manually by adjustment of a dial. Further, memory means are provided to store the counts related to specific time periods, and with a suitable display, these counts may be viewed, as appropriate. The subject may also use a response chart and record the number of counts in the predetermined time period, such as during a night, in order to ascertain the progress he is making. The aversive stimulus may be terminated automatically or manually, as desired, with manual termination requiring the sleeper to change his position, which is more desirable from a behavior modification standpoint.

An important feature of the present invention is the provision of a register in order to unalterably produce a count which cannot be questioned by the subject when he awakes. In this manner, the subject will be clearly aware every morning of whether or not his performance is improving. Provision of the register eliminates the possibility that the subject could "fool" himself by believing his performance (snoring) was improving, even though it was not. The provision of the memory means in combination with the register allows the subject to review his progress, and further, without such a memory means, a suitable recording technique can be employed to allow the operator to check his progress.

The register also serves as part of a biofeedback or behavior shaping mechanism. Thus, the subject is actively involved in lowering the threshold level required to trigger the alarm as determined by his improving performance. This shaping provides significant positive reinforcement for the subject continuing to improve.

DETAILED DESCRIPTION

Figure 1:
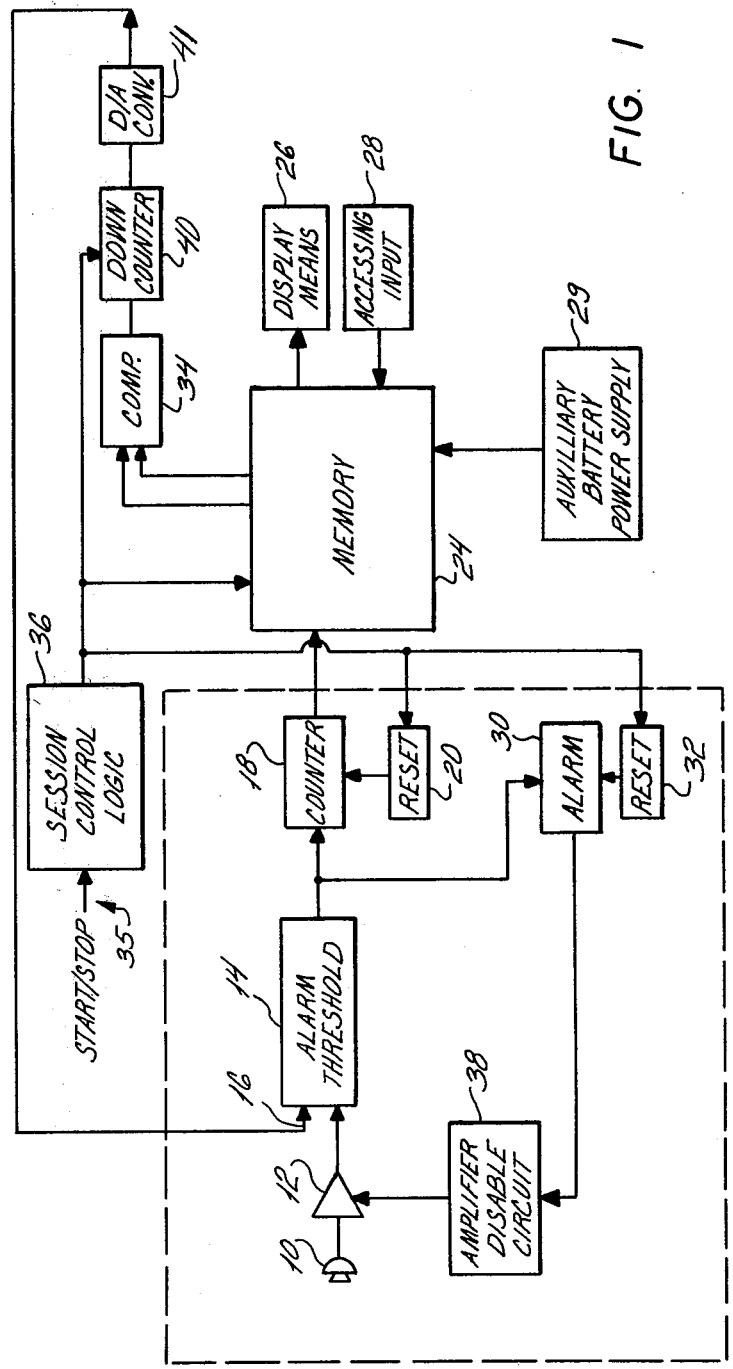
FIG. 1 is a block diagram illustrating an embodiment of the subject invention.

In accordance with the principles of the present invention, a behavior shaping device is provided for eliminating nocturnal sounds emanating from a sleeper. These sounds may be the conventional snoring or bruxism, but may be other sounds. The block diagram of FIG. 1 illustrates an embodiment of the present invention that will be discussed in more detail hereinafter.

A microphone 10 or other suitable transducer device is provided to sense sounds within a certain area, such as a bedroom, and an output signal is produced and passed through an amplifier 12 into one input of a two input alarm threshold and averaging network device 14. The alarm threshold device can be any suitable device which provides an output signal when the output of amplifier 12 is greater than a predetermined trigger level, which is set by the second input 16. The trigger level may be set manually or automatically, as desired, and upon the sensing of a signal from amplifier 12 being greater than the level set by trigger level 16, an output signal will be produced at the output of alarm threshold device 14. A counter or register 18 is provided which receives the output of alarm threshold 14 and provides a count of the number of such pulses produced. The counter is resettable by reset means 20 which may be either manual or automatic. The output of the counter is supplied to a memory 24 which stores the count in counter 18, and the memory 24 may supply its output to a display means 26 connected thereto under control of an accessing input 28.

The memory device 24 may be a low power CMOS type which will retain its information, even if the unit is unplugged between sessions, by using an auxiliary battery power supply 29.

As one embodiment of the instant invention, the above described components are used together with an alarm 30, the alarm being triggered upon the generation of an output signal by alarm threshold 14 causing the sleeper to be disturbed. Alarm 30 may be reset manually or automatically by alarm reset 32, and if manually, then the sleeper will have to awaken, reach over, and push the alarm reset lever. As is well known, it is preferable for the sleeper to have to move his position for positive behavior modification to be enhanced.

The behavior shaping apparatus already described may be used by a sleeper who sets the trigger level prior to going to sleep, and if awakened during the sleep, will reset the alarm 30 by means of alarm reset 32. In the morning when the sleeper awakes, he may observe the count in display means 26 in order to determine the number of output signals generated by alarm threshold 14 during the predetermined time period, that is, during the time when the subject was sleeping. The subject may maintain a log indicating the number of such output signals, and if he finds that the number of such output signals decreases on successive nights, the subject will decrease the trigger level 16 in order to further enhance the positive behavior being achieved. The significance of the counter register and display means is to ensure that the subject is not able to "fool" himself by believing that he did not trigger the alarm threshold during the sleeping period. This unalterable counting mechanism is unassailable evidence of the progress and behavior of the subject and is the feedback between the subject and the device serving to shape the behavior of the subject.

As another embodiment of our invention, the above described behavior modification device may be automated, and to that end, the outputs of memory 24 may be supplied to a two input comparator 34. At the start of any period, usually the evening session, the subject can manually activate a start of session control logic block 36, which is formed of conventional digital logic circuits, whose functions will be described hereinafter.

The details of those circuits are clear to one of ordinary skill in the art once the control functions are described. Initially, the logic block 36 which is connected to reset 20 causes counter 18 to be reset. The logic block 36 is also connected to reset 32 which causes alarm 30 to be inhibited and through said alarm 30 an amplifier disable circuit 38 to disable amplifier 12 for a period of time to allow the subject to settle in bed.

The memory 24 is capable of storing counts for a large number of time periods, and in particular, in one embodiment the counts from the two previous nights are supplied to comparator 34. If there has been an improvement (night 2 less than night 1) a signal is generated which is supplied to a down counter 40, stepping down the count therein. A D/A converter 41 is connected to the output of counter 40, and a new D/C level is supplied to input 16 of alarm threshold 14. At the end of the evening session, the subject can activate the start/stop switch 35, which causes the contents of counter 18 to be supplied to memory 24.

As described above, the subject may maintain a log of his somnolant activity, but as another feature of the instant invention, the memory device 24 is capable of storing counts accumulated in counter 18 during respective time periods. The memory 24 has an accessing input 28 enabling it to access information in any of the storage locations in the memory, and a display means 26 is provided as an output of programmable memory device to display the contents of the memory location accessed by accessing input 28. The display device may be able to display the subject's performance for any period of time, such as a week, month, or the like.

Figure 2:
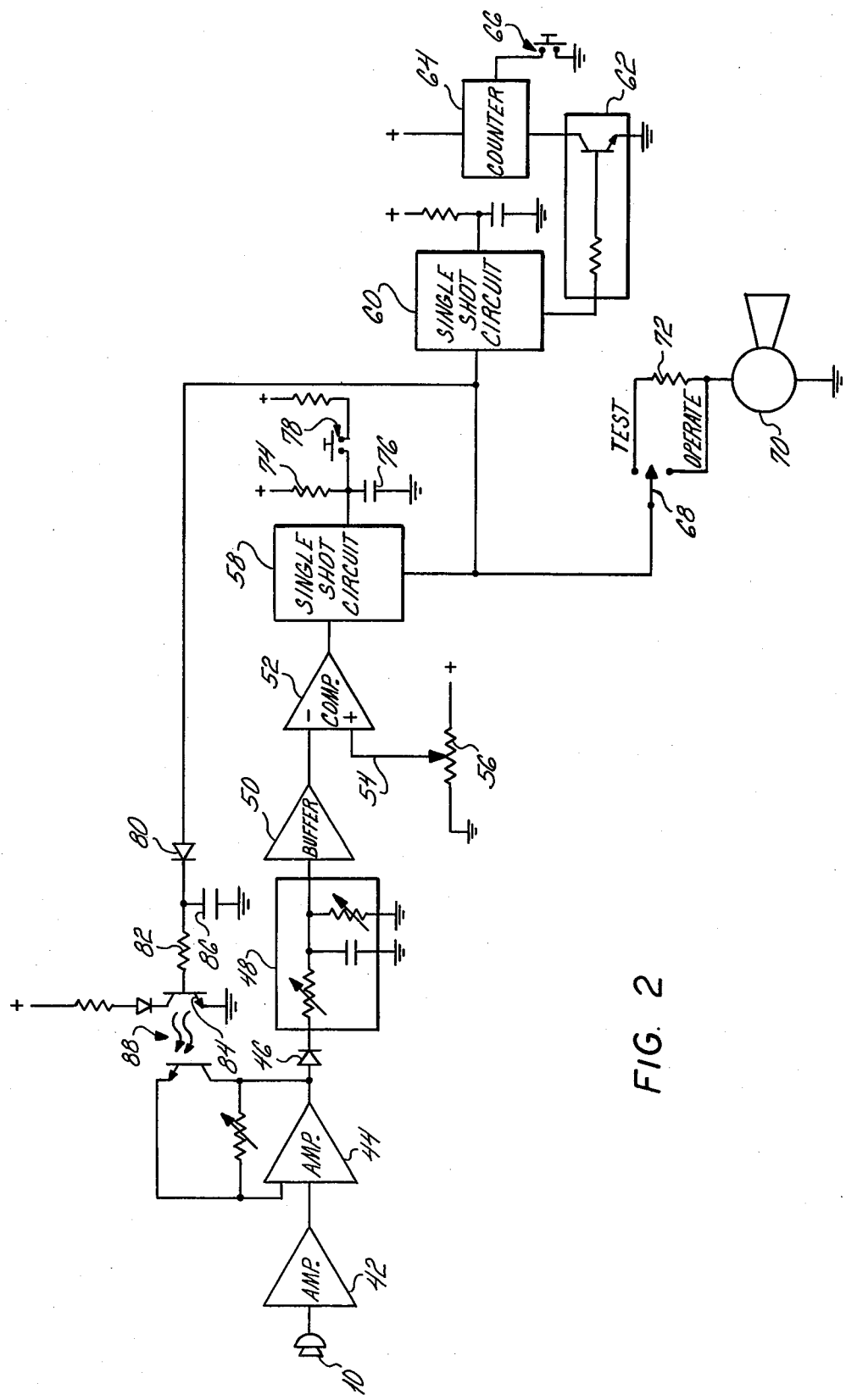
FIG. 2 is a circuit diagram illustrating another embodiment of the present invention.

Referring now to FIG. 2, there is shown a circuit diagram of an embodiment of the instant invention which is presented without the programmable memory device 24 the display means 26, the session controlled logic 36 and the comparator 34. The same numbers are used in FIG. 2 as in FIG. 1, where appropriate. The output of microphone 10 is supplied through a first amplifier 42 to a second amplifier 44 which are type 741's. These amplifiers are operational amplifiers and are well known in the art. The output of amplifier 42 serves as one input to amplifier 44, while the second input to amplifier 44 comprises a means to damp unwanted output signals from microphone 10 as will be described hereinafter. The output of amplifier 44 passes through a diode 46 into an averaging network 48, which may be internally adjustable. The output of averaging network 48 is supplied through another type 741 amplifier as one input to a 2-input operational amplifier 52. The second input 54 to operational amplifier 52 is variable which may be manually set and comprises a potientiometer 56 with wiper arm thereof serving as the input 54 to operational amplifier 52. When the output of buffer 50 is greater than the threshold level set at the input 54 of operational amplifier 52, a signal is produced (output signal) which triggers a single shot circuit 58 (type 555) which supplies an output to a single shot circuit 60 (type 555) the output of which is supplied through a current amplifier 62 to counter 64, which may be an electromechanical counter produced by Sodeco Company. The counter 64 displays the count registered therein, and there is also provided a manual zero reset 66 for resetting the counter.

The output of single shot 58 is also supplied through switch 68 which is settable to either a test or operate position, and when placed in the operate position triggers alarm 70 which is a Mallory Sonalert audio alarm.

When placed in the test position, a limit resistor 72 is provided to ascertain that the triggering circuitry operates and limits the volume produced by alarm 70.

A timing circuit comprising a resistor 74 and capacitor 76 is connected to control the time that single shot 58 remains on and is operating alarm 70. The alarm will stay on for no longer than that predetermined period of time, which may be one or two minutes, as desired. If the subject awakens prior to the expiration of the time period, manual alarm reset means 78 may be employed to reset single shot 58.

As another feature of this invention, means are provided to prevent the triggering circuitry from activating until the sleeper has returned to bed and finished moving around. To that end, the output of single shot 58 is also supplied through a delay circuit comprising a diode 80 connected through resistor 82 to the base input of a transistor 84. The cathode of diode 80 is also supplied through a capacitor 86 to ground. When single shot 58 produces its output signal, transistor 84 is conducting and an optocoupler 88 is provided between the transistor 84 and the second input circuit to operational amplifier 44. After transistor 84 turns off due to the time period determined by resistor 82 and capacitor 86, the optocoupler 88 is no longer operative. While operative the output from amplifier 44 supplied to the half wave rectifier 46 and averaging network 48, cannot swing positive so as to charge the averaging network because of the conducting optocoupler 88 in the feedback loop of amplifier 44, so that during that time period, any signals emanating from microphone 10 will not pass through to comparator 52. It may thus be seen that while the sleeper returns to bed, his initial movements in getting comfortable will not allow the behavior modification device alarm 70 to be retriggered.

It will thus be seen that the objects set forth, among those made apparent from the preceding description, are efficiently attained and, since certain changes may be made in the above behavior modification device without departing from the scope of the invention, it is intended that all matter contained in the above description and shown in the accompanying drawings shall be interpreted as illustrative and not in a limiting sense.

What is claimed is:

1. A behavior modification device for eliminating nocturnal sounds emanating from a sleeper, said device comprising:
    transducer means responsive to sounds emanating from a sleeper of at least a predetermined level of loudness to produce an output alarm signal,
    means responsive to said output alarm signal for producing aversive stimulus each time said predetermined level is exceeded causing said sleeper to awake each such time,
    means for terminating said aversive stimulus,
    register means connected to receive said output alarm signal and to register the total number of said output alarm signals generated in a predetermined period of time, and
    display means connected to said register means for visibly displaying the total number of said output alarm signals generated in said predetermined period of time, whereby a credible record of the number of sounds emanating from said sleeper is established.

2. A behavior modification device as set forth in claim 1, further comprising amplitude sensitive output signal producing means for producing said output alarm signal when said sounds exceed said predetermined level, and adjustable input level means for changing said predetermined level.

3. A behavior modification device as set forth in claim 2, comprising comparator means connected to said register means for comparing the total number of said output alarm signals generated in one predetermined time period with the number generated in a prior time period, and control means connected between said comparator and said adjustable input level means to decrease said predetermined level when the total number of said output alarm signals generated in a present predetermined time period is less than a prior time period.

4. A behavior modification device as set forth in claim 3, further comprising proportioning means connected to the output of said comparator for generating a signal having an amplitude directly proportional to the difference in compared total counts, said proportioning means adjusting said predetermined level directly proportional to the difference in compared total counts.

5. A behavior modification device as set forth in claim 2, wherein said adjustable input level is manually adjustable enabling the subject to reduce the predetermined level as the total number of said output alarm signals decreases in said predetermined periods of time.

6. A behavior modification device as set forth in claim 1 further comprising manually actuable means connected to said means for producing said aversive stimula for terminating said aversive stimula.

7. A behavior modification device as set forth in claim 1, further comprising electronic memory means connected to said register means, said memory means adapted to store the count in said register means representing said total number of said output signals generated, and means coupled to said memory means for addressing said memory means and retrieving any count stored therein.

8. A behavior modification device as set forth in claim 7, wherein said memory means further comprises means to store signals representative of each predetermined period of time.

9. A behavior modification device as set forth in claim 7, further comprising display means connected to said memory means for visibly displaying the contents of said memory means.

10. A behavior modification device as set forth in claim 1, wherein said register means comprises zero reset means for resetting said register means when the contents thereof are read.

11. A behavior modification device as set forth in claim 10, wherein said zero reset means comprises manually actuable means.

12. A method for achieving behavior modification to eliminate nocturnal sounds emanating from a sleeper, the method comprising:
    triggering an alarm each time the sounds emanating from the subject exceed a predetermined level,
    terminating said alarm,
    counting the number of said sounds sensed during a predetermined period of time,
    and visually displaying the count representing the number of times the sound is sensed, whereby the sleeper sees credible evidence of the production of nocturnal sounds.

13. The method set forth in claim 12, further comprising the step of adjusting said predetermined level responsive to the number of sounds sensed as compared to the number of sounds sensed in a prior predetermined period of time.

14. The method as set forth in claim 12, further comprising the step of storing said number of time the sound was sensed in a prior predetermined period of time.

* * * * *